US012788346B2

(12) United States Patent
Miyachi

(10) Patent No.: US 12,788,346 B2
(45) Date of Patent: Nov. 10, 2026

(54) RADIATION IMAGING APPARATUS, RADIATION IMAGING SYSTEM, METHOD OF OPERATING RADIATION IMAGING APPARATUS, AND MEDIUM

(71) Applicant: CANON KABUSHIKI KAISHA, Tokyo (JP)

(72) Inventor: Norihiko Miyachi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 139 days.

(21) Appl. No.: 18/888,997

(22) Filed: Sep. 18, 2024

(65) Prior Publication Data

US 2025/0099057 A1 Mar. 27, 2025

(30) Foreign Application Priority Data

Sep. 21, 2023 (JP) ................................ 2023-156560
Jul. 19, 2024 (JP) ................................ 2024-115665

(51) Int. Cl.
*A61B 6/00* (2024.01)

(52) U.S. Cl.
CPC ................ *A61B 6/487* (2013.01); *A61B 6/54* (2013.01)

(58) Field of Classification Search
CPC ................................ A61B 6/487; A61B 6/54
See application file for complete search history.

(56) References Cited

U.S. PATENT DOCUMENTS 8,785,863 B2 7/2014 Oda
2014/0021360 A1* 1/2014 Oda .......................... G01T 1/17 250/361 R

FOREIGN PATENT DOCUMENTS

JP 2014-20971 A 2/2014
JP 2018-192062 A 12/2018

OTHER PUBLICATIONS

JP 2018-192062 A and its English translation. (Year: 2018).*

* cited by examiner

*Primary Examiner* — Chih-Cheng Kao
(74) *Attorney, Agent, or Firm* — VENABLE LLP

(57) ABSTRACT

To allow a radiation imaging apparatus to perform imaging processing of determining the end of fluoroscopy without performing synchronous communication to and from a radiation generation apparatus, the radiation imaging apparatus includes: a radiation detection unit which includes a plurality of pixels for radiation detection arranged therein and which is to be used for generation of image data based on radiation applied to the radiation detection unit; and a determination unit configured to determine that irradiation of the radiation has stopped when a reduction amount of an irradiation amount of the radiation obtained from a detection pixel included in the plurality of pixels is larger than a reduction threshold value.

11 Claims, 5 Drawing Sheets

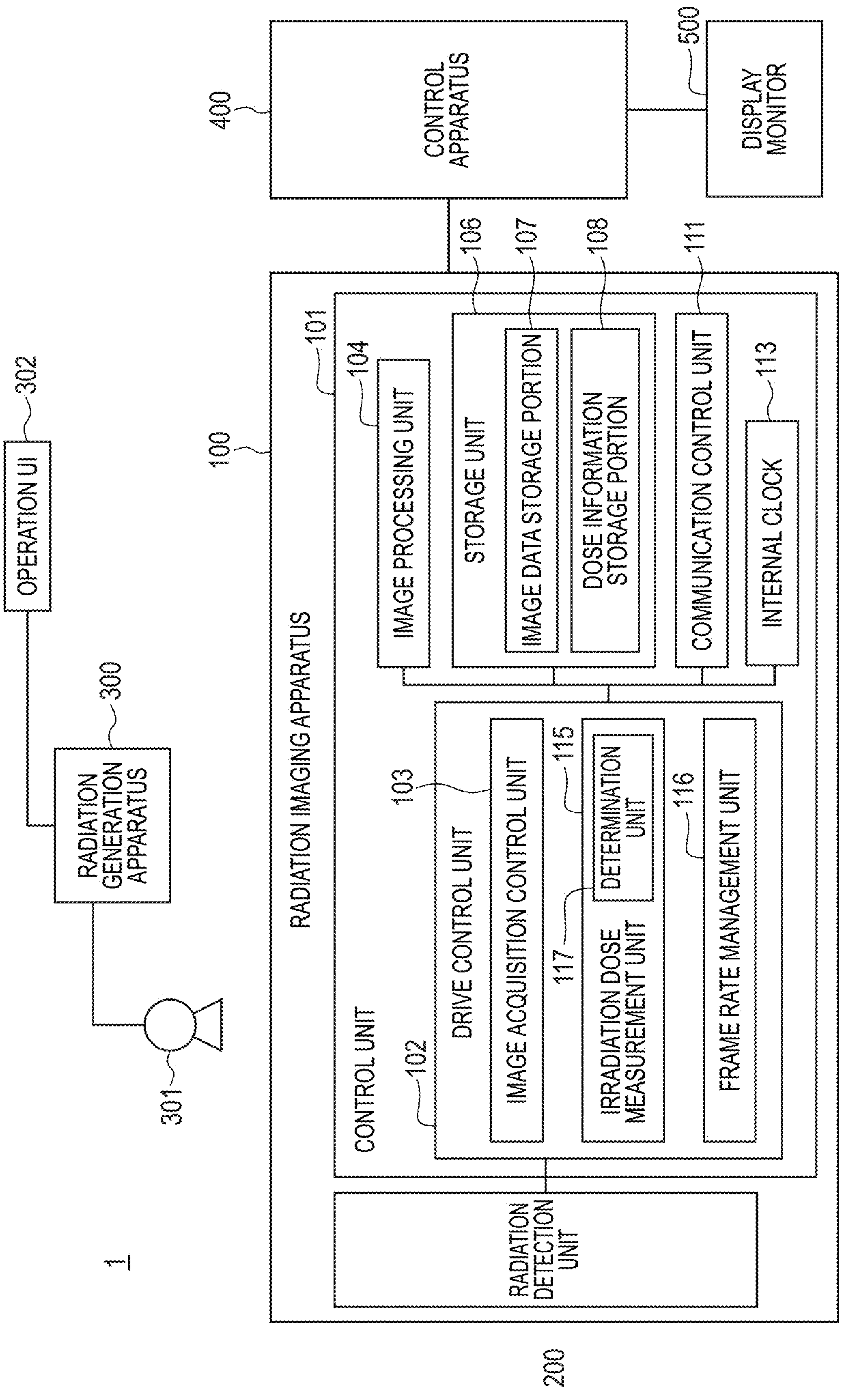
1
OPERATION UI
302
RADIATION GENERATION APPARATUS
300
301
CONTROL APPARATUS
400
DISPLAY MONITOR
500
100
RADIATION IMAGING APPARATUS
101
CONTROL UNIT
102
DRIVE CONTROL UNIT
103
IMAGE ACQUISITION CONTROL UNIT
IRRADIATION DOSE MEASUREMENT UNIT
117
DETERMINATION UNIT
115
FRAME RATE MANAGEMENT UNIT
116
IMAGE PROCESSING UNIT
104
STORAGE UNIT
106
IMAGE DATA STORAGE PORTION
107
DOSE INFORMATION STORAGE PORTION
108
COMMUNICATION CONTROL UNIT
111
INTERNAL CLOCK
113
RADIATION DETECTION UNIT
200

RADIATION IMAGING APPARATUS, RADIATION IMAGING SYSTEM, METHOD OF OPERATING RADIATION IMAGING APPARATUS, AND MEDIUM

BACKGROUND OF THE INVENTION

Field of the Invention

The present disclosure relates to a radiation imaging apparatus, a radiation imaging system, a method of operating a radiation imaging apparatus, and a medium.

Description of the Related Art

There has been known a radiation imaging apparatus that performs moving-image photographing while performing synchronous communication to and from a radiation generation apparatus. Connection of a communication cable used at the time of synchronous communication is troublesome, and thus hinders the flexibility of system upgrades in a moving-image rounding cart and the like. In contrast, there has also been known presence of a radiation imaging apparatus that performs still-image photographing without performing synchronous communication. In this radiation imaging apparatus, a user can perform photographing without restriction of a photographing location due to a cable length.

When no synchronous communication is performed, the radiation generation apparatus and the radiation imaging apparatus are required to perform processing at the same timing, and, in order to perform continuous fluoroscopy, it is required to determine start and end timings of the photographing. In Japanese Patent Application Laid-Open No. 2018-192062, there is disclosed a radiation imaging apparatus that performs still-image photographing without performing synchronous communication. In this radiation imaging apparatus, a bias power supply of a power supply circuit is used to perform standby drive for detection of radiation irradiation, and the photographing is started in response to the detection of the radiation irradiation. Further, in Japanese Patent Application Laid-Open No. 2014-020971, there is disclosed a radiation imaging apparatus that determines start and end of radiation irradiation based on a change in charge output signal of a radiation detection element to perform an accumulation (irradiation start) operation and a readout (irradiation end) operation.

In the radiation imaging apparatus as disclosed in Japanese Patent Application Laid-Open No. 2018-192062, it is required to perform the standby drive for detection of the radiation irradiation before the photographing. Accordingly, it is not easy to adapt to processing of continuously performing a photographing operation such as continuous fluoroscopy. Further, also in the radiation imaging apparatus as disclosed in Japanese Patent Application Laid-Open No. 2014-020971, it is not easy to adapt to processing of continuously performing a photographing operation such as continuous fluoroscopy.

SUMMARY OF THE INVENTION

In view of the above, one of objects of the present disclosure is to allow a radiation imaging apparatus to perform imaging processing of determining the end of fluoroscopy without performing synchronous communication to and from a radiation generation apparatus.

In order to achieve the above-mentioned object, a radiation imaging apparatus according to one embodiment of the present invention includes: a radiation detection unit which includes a plurality of pixels for radiation detection arranged therein and which is to be used for generation of image data based on radiation applied to the radiation detection unit; and a determination unit configured to determine that irradiation of the radiation has stopped when a reduction amount of an irradiation amount of the radiation obtained from a detection pixel included in the plurality of pixels is larger than a reduction threshold value.

Further features of the present invention will become apparent from the following description of exemplary embodiments with reference to the attached drawings.

BRIEF DESCRIPTION OF THE DRAWINGS

FIG. 1 is a block diagram for illustrating a configuration example of a radiation imaging system according to a first embodiment of the present disclosure.

DESCRIPTION OF THE EMBODIMENTS

Figure 2:
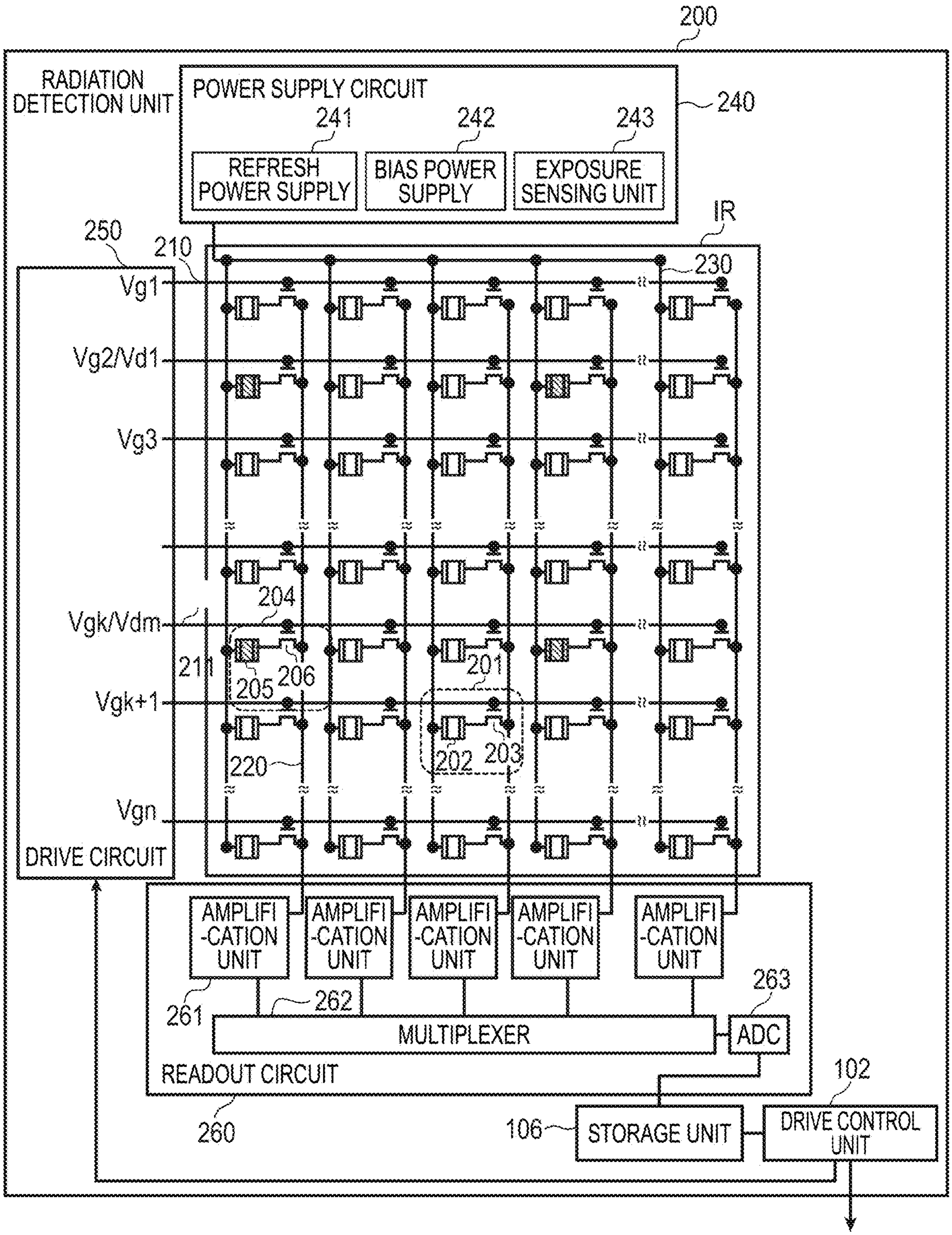
FIG. 2 is a block diagram for illustrating a configuration example of a radiation detection unit in the radiation imaging system of FIG. 1.

Now, a radiation imaging apparatus, a radiation imaging system including the radiation imaging apparatus, and a method of operating the radiation imaging apparatus according to embodiments of the present disclosure are described with reference to the drawings. The embodiments described below do not limit the present disclosure set forth in the appended claims. A plurality of features are described in the embodiments, but the present disclosure does not necessarily require all of those plurality of features, and a plurality of features may be combined as appropriate.

Moreover, the dimensions, materials, shapes, relative positions of components, and the like described in the following embodiments can be freely selected, and can be changed in accordance with various conditions or a configuration of an apparatus to which the present disclosure is applied. Further, in the drawings, identical or similar configurations are denoted by the same reference symbols, and duplicate descriptions thereof are omitted. Further, in the following description, X rays are exemplified as radiation, but examples of the radiation to which the present disclosure is applicable include a rays, B rays, y rays, particle beams, and cosmic rays.

First Embodiment

Now, as a first embodiment of the present disclosure, a schematic configuration of a radiation imaging system including a radiation imaging apparatus according to the present disclosure and processing of operating the radiation imaging apparatus to be carried out are described with reference to FIG. 1 to FIG. 4 of the accompanying drawings.

Configuration of Radiation Imaging System of First Embodiment

FIG. 1 shows a configuration example of a radiation imaging system according to the first embodiment. A radiation imaging system 1 includes a radiation imaging apparatus 100 including a radiation detection unit 200, and a control apparatus 400 which is a processing apparatus for acquiring image data from the radiation imaging apparatus 100 to process the acquired image data. It is preferred that the radiation imaging system 1 further include a radiation source 301 for applying radiation, and a radiation generation apparatus 300 for controlling the radiation source 301. Further, the radiation imaging system 1 can include an operation user interface (UI) 302 for allowing a user to operate the radiation generation apparatus 300. The radiation imaging apparatus 100 can be connected to the above-mentioned control apparatus 400 and a display monitor 500.

The radiation imaging apparatus 100 includes the radiation detection unit 200 for detecting radiation to generate image data, and a control unit 101 for controlling photographing and a communication operation. The control unit 101 controls the entire radiation imaging apparatus. The control unit 101 includes a drive control unit 102, an image processing unit 104, a storage unit 106, a communication control unit 111, and an internal clock 113. The drive control unit 102 controls drive of the radiation detection unit 200 and acquisition of a radiation image, and includes an image acquisition control unit 103, an irradiation dose measurement unit 115, and a frame rate management unit 116. The image acquisition control unit 103 acquires an amount of electric charges accumulated due to the irradiation of radiation, which is obtained when the radiation is applied under a state in which each pixel of the radiation detection unit 200 to be described later can accumulate electric charges. This amount of electric charges is read out by the irradiation dose measurement unit 115 as image data to be used for generation of the radiation image. Further, the irradiation dose measurement unit 115 further includes a determination unit 117, and the determination unit 117 performs large/small determination between a radiation dose obtained from a detection pixel 204 and a detection drive line 211, which are to be described later, and an increase amount and a reduction amount of the radiation dose determined in advance. The determination performed by the determination unit is not limited to the large/small determination with respect to the increase amount and the reduction amount of the radiation dose, and may be determination of an increase and a decrease in change rate of the radiation dose, comparative determination between the radiation dose and a threshold value, or other publicly-known determination methods. The frame rate management unit 116 manages a photographing period of the fluoroscopy.

The image processing unit 104 performs image processing on the image acquired from the radiation detection unit 200. The storage unit 106 includes an image data storage portion 107 for storing the acquired image data, and a dose information storage portion 108 for storing dose information corresponding to the photographing. The storage unit 106 is formed of a volatile memory. The communication control unit 111 controls communication between the radiation generation apparatus 300 and the control unit 101. The internal clock 113 is used for acquiring a photographing time, an elapsed time period, or the like. The image data or the like stored in the storage unit 106 is transmitted to the control apparatus 400, and is subjected to further image processing or analysis of the image data as required, and then the result is displayed on the display monitor 500.

The photographing period (hereinafter referred to as "frame rate") managed by the frame rate management unit 116 is registered before the fluoroscopy is carried out by the radiation imaging apparatus 100. At this time, as a method for registration, the frame rate may be transmitted from the control unit 101 and this frame rate may be registered, or a screen for inputting the frame rate may be displayed on the display monitor 500 so that the user may directly input the frame rate via this screen. Further, the method of registering the frame rate is not limited to those methods, and may be achieved by other publicly-known methods.

Here, the control unit 101 can be formed of a computer provided with a processor and a memory. The control unit 101 may be formed of a general computer, or may be formed of a computer dedicated to the radiation imaging system. Further, the control unit 101 may be combined with the control apparatus 400 and the display monitor 500 to be, for example, a personal computer, and a desktop PC, a laptop PC, a tablet PC (mobile information terminal), or the like may be used. Moreover, the control apparatus 400 may be formed as such a cloud-type computer that a part of components is arranged in an external apparatus.

Further, each component other than the storage unit 106 of the control unit 101 may be formed of, for example, a software module to be executed by a processor such as a central processing unit (CPU) or a micro processing unit (MPU) provided in the control apparatus 400. The processor may be, for example, a graphical processing unit (GPU), a field-programmable gate array (FPGA), or the like. Further, the each component may be formed of a circuit or the like implementing a specific function, such as an ASIC. The storage unit 106 may be formed of any storage medium such as an optical disc or a memory, such as a hard disk drive accompanying the control apparatus 400.

The display monitor 500 can be formed of any display or the like, and displays, in accordance with the control of the control apparatus 400, various images and various types of information such as information of a person to be inspected, and a mouse cursor or the like responding to the user's operation. The display monitor 500 can be used as an input device for giving an instruction to the control unit 101, and, specifically, can be accompanied by a keyboard and a mouse. The display monitor 500 may be formed of a touch panel display. Further, a function of the operation UI 302 to be described later may be implemented by a touch panel of the display monitor 500.

<Radiation Generation Apparatus>

The radiation generation apparatus 300 includes the operation UI 302 for operating the radiation generation apparatus 300. The user performs setting of irradiation conditions of the radiation, or the like, via the operation UI 302. In response to this operation, the radiation generation apparatus 300 continuously applies radiation in a pulse form. In the present disclosure, no wired connection for exchanging synchronous signals such as notification of start and end of radiation irradiation and notification of radiation irradiation possible timings is established between the radiation generation apparatus 300 and the radiation imaging apparatus 100.

<Radiation Detection Unit>

Next, with reference to FIG. 2, the radiation detection unit 200 in this embodiment is described. FIG. 2 shows an example of a configuration of the radiation detection unit 200. The radiation detection unit 200 includes an imaging region IR in which a plurality of pixels for radiation detection are arranged, a power supply circuit 240 connected to the imaging region IR, a drive circuit 250, and a readout circuit 260. In the imaging region IR, a plurality of pixels are arranged so as to form a plurality of rows and a plurality of columns, and the plurality of pixels receive irradiation of pulsed radiation applied by the radiation generation apparatus 300 to generate electric charges. A plurality of drive lines 210 connecting the drive circuit 250 and the pixels to each other are each arranged so as to correspond to any one pixel row among the plurality of pixel rows. A plurality of signal lines 220 connecting the readout circuit 260 and the pixels to each other are each arranged so as to correspond to any one pixel column among the plurality of pixel columns. The readout circuit 260 includes amplification units 261 corresponding to the respective signal lines 220, a multiplexer 262 connected to those amplification units 261, and an analog-digital conversion circuit (analog-digital converter: hereinafter referred to as "AD converter") 263.

<Pixel for Irradiation Dose Monitoring>

The plurality of pixels arranged in the imaging region IR include a plurality of imaging pixels 201 to be used for acquiring a radiation image, and one or more detection pixels 204 to be used for monitoring the irradiation dose of the radiation.

<Acquisition of Image Using Plurality of Pixels>

The imaging pixel 201 includes a conversion element 202 for converting radiation into an electrical signal, and a switching element 203 for connecting the corresponding signal line 220 and the conversion element 202 to each other. The detection pixel 204 includes a conversion element 205 for converting radiation into an electrical signal, and a switching element 206 for connecting the corresponding signal line 220 and the conversion element 205 to each other. The detection pixel 204 is arranged so as to be included in a row and a column each formed of a plurality of imaging pixels 201. In FIG. 2, the imaging pixel 201 and the detection pixel 204 are distinguished from each other by hatching the conversion element 202 and the conversion element 205 differently from each other. In the illustrated example, the detection pixel 204 is arranged in the same row and column among the rows and columns in which the imaging pixels 201 are arranged, but the arrangement of the detection pixel 204 is not limited to this example. It is only required that at least one detection pixel 204 be arranged in the imaging region IR.

The conversion element 202 and the conversion element 205 may each be formed of a scintillator for converting radiation into light and a photoelectric conversion element for converting light into an electrical signal. The scintillator is generally formed into a sheet shape so as to cover the imaging region IR, and is shared by a plurality of pixels. In place thereof, the conversion element 202 and the conversion element 205 may each be formed of a conversion element for converting radiation directly into an electrical signal. Further, the switching element 203 and the switching element 206 may each include, for example, a thin film transistor (TFT) including an active region formed of a semiconductor such as an amorphous silicon or a polycrystalline silicon. The detection pixel 204 also has a pixel configuration similar to that of the imaging pixel 201, and is connected to the corresponding drive line 210 and the corresponding signal line 220. The imaging pixel 201 may be connected to the same signal line 220 as that of the detection pixel 204.

<Radiation Detection>

A bias line 230 is connected to the power supply circuit 240. The power supply circuit 240 includes, in the circuit, a refresh power supply 241, a bias power supply 242, and an exposure sensing unit 243, and is configured to sense a change in bias current at the time of radiation irradiation. In more detail, the power supply circuit 240 is driven by the drive control unit 102 to cause the exposure sensing unit to sense the change in the bias current supplied to the conversion elements 202 and 205 via the bias line 230 at the time of radiation irradiation. In the first embodiment, a unit including a current-voltage conversion circuit including an operational (OP) amplifier and a resistance, and an AD converter for converting the converted voltage into a digital value is used as the exposure sensing unit. However, a mode of the exposure sensing unit is not limited to this example, and other publicly-known current-voltage conversion circuits may be used, or an output voltage of the current-voltage conversion circuit may be directly used. Further, current information output from the bias line 230 may be directly used. The control unit 101 is notified of the change in the bias current sensed by the power supply circuit 240 through use of the exposure sensing unit, that is, information on the start of the radiation irradiation obtained in correspondence therewith.

The power supply circuit 240 also supplies a refresh voltage from the refresh power supply 241 to the conversion elements 202 and 205 via the bias line 230. The refresh voltage is applied to those elements during a period of a refresh operation in the conversion elements 202 and 205, and a bias voltage for obtaining the change in bias current described above is applied to those conversion elements in other periods.

<Detection Line Using Pixel for Irradiation Dose Monitoring>

Next, an operation of measuring the radiation dose through use of the radiation detection unit 200 is described. The drive circuit 250 supplies a drive signal to pixels to be driven through a plurality of drive lines 210 in accordance with a control signal from the drive control unit 102. When the pixel to be driven is supplied with the drive signal, a signal accumulated in the conversion element of this pixel is brought to a state readable by the readout circuit 260. In this case, when the drive line 210 is connected to at least one detection pixel 204, this drive line 210 is referred to as "detection drive line 211." The drive control unit 102 successively repeats readout of only the pixels in a pixel row connected to the detection drive line 211 including the detection pixel 204 while controlling the imaging pixels 201 into an accumulating state, to thereby monitor the change in irradiation dose. In addition, the irradiation dose measurement unit 115 measures an increase and a decrease in irradiation dose based on the dose information that is repeatedly read out.

<Radiation Photographing>

The readout circuit 260 is configured to read out signals from a plurality of pixels through a plurality of signal lines 220. As described above, the readout circuit 260 includes the plurality of amplification units 261, the multiplexer 262, and the AD converter 263. Each of the plurality of signal lines 220 is connected to a corresponding amplification unit 261 among the plurality of amplification units 261 of the readout circuit 260. One signal line 220 corresponds to one amplification unit 261. The multiplexer 262 selects one of the plurality of amplification units 261 in a predetermined order, and supplies a signal supplied from the selected amplification unit 261 to the AD converter 263. The AD converter 263 converts the supplied signal to a digital signal. The image data converted to a digital value is stored in the storage unit 106 in FIG. 1.

The image acquisition control unit 103 acquires a radiation image that is based on the image data acquired through irradiation of radiation, and an image such as an offset image that is based on the image data acquired without irradiation of radiation. In more detail, the image acquisition control unit 103 reads out the image data obtained by applying radiation during accumulation of each pixel, and causes the storage unit 106 to hold the image data as a radiation image. This operation is successively carried out to allow photographing of a radiation image as a moving image.

With the processing described above being executed, from the irradiation of the radiation by the radiation generation apparatus 300 to the radiation imaging apparatus 100, electric charges corresponding to the radiation are accumulated, and the electric charges are read out so that one still image is obtained. Meanwhile, in moving-image photographing, when the irradiation of the radiation is performed at a timing at which the radiation imaging apparatus 100 cannot acquire an image, the radiation causes invalid exposure and becomes harmful to a person to be inspected. Thus, the moving-image photographing can be performed by regularly and alternately repeating irradiation of radiation for acquiring a radiation image and readout of electric charges. In the moving-image photographing, performance of one radiation irradiation and readout of electric charges is regarded as one frame processing. It is required to regularly maintain the frame processing during the radiation irradiation, and perform start and stop of the series of alternate operations.

<Photographing Processing>

Figure 3:
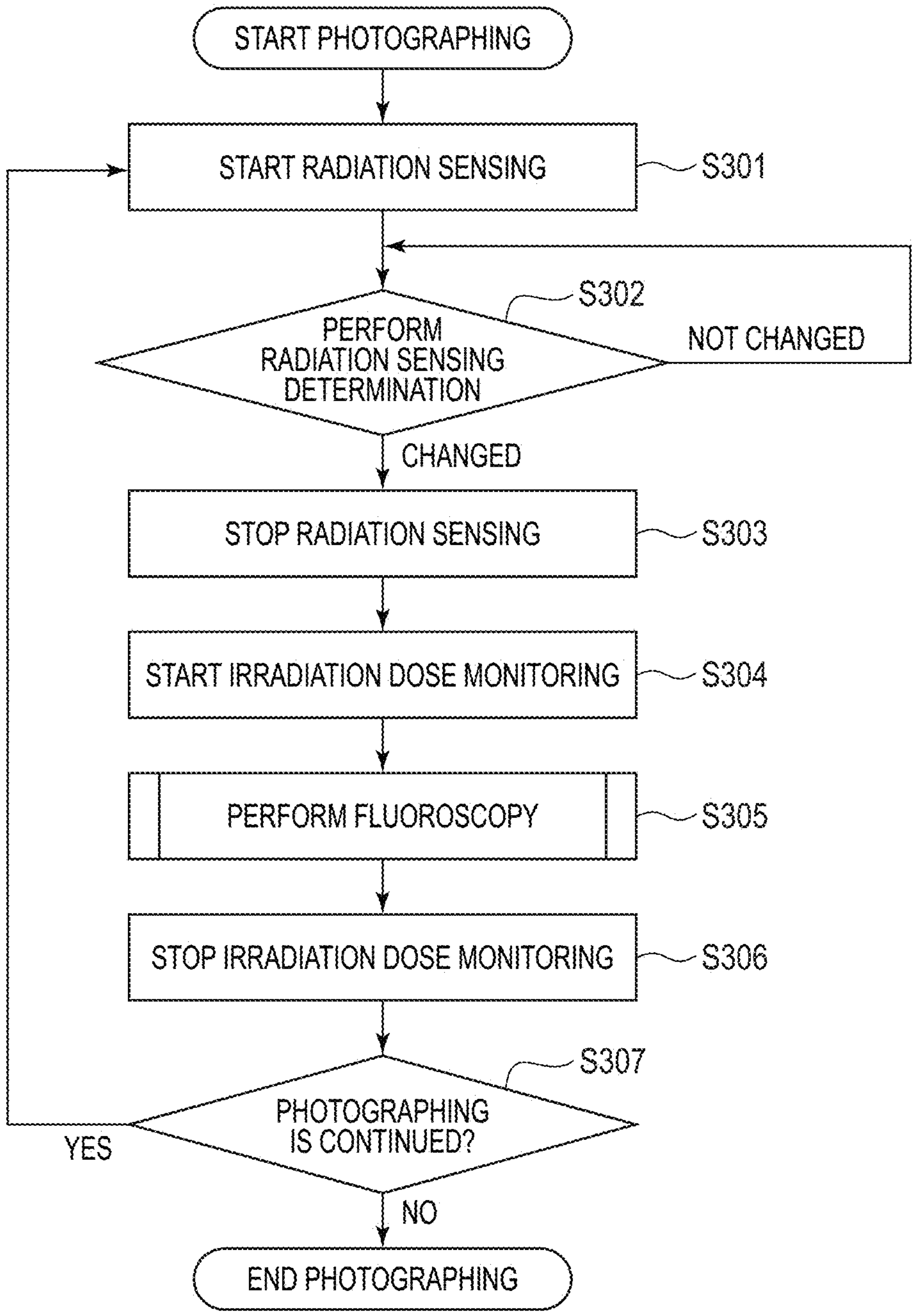
FIG. 3 is a flow chart for illustrating a series of photographing operations executed at the time of fluoroscopy using pulse irradiation in the first embodiment.

Next, a photographing operation using the radiation generation apparatus 300 and the radiation imaging apparatus 100 in the first embodiment is described with reference to FIG. 3. FIG. 3 is a flow chart for illustrating a series of operations to be executed by the control unit 101 at the time of fluoroscopy performed through irradiation of radiation in the first embodiment. Although not shown, in the photographing processing described below, a subject such as a person is arranged between the radiation source 301 and the radiation detection unit 200. In addition, the radiation applied from the radiation source 301 is transmitted through this subject, and the radiation detection unit 200 detects the radiation transmitted through the subject or the radiation not transmitted through the subject.

<From Activation of Imaging Apparatus to Photographing Standby>

For example, in response to power-on of the radiation imaging apparatus 100 as a trigger, the control unit 101 executes a photographing preparation operation, and the photographing operation described below is started. When the photographing operation is started, first, in Step S301, the control unit 101 starts radiation sensing using the power supply circuit 240, more specifically, the exposure sensing unit 243. Specifically, the sensing of the change in current in the bias line 230 by the exposure sensing unit 243 is started as described above. The power supply circuit 240 sequentially performs the refresh operation and the processing of sensing the change in current in the bias line 230 for each pixel column. The processing of sensing the current change due to the radiation irradiation in Step S302 is regularly repeated until the radiation is applied to the radiation imaging apparatus 100 by the radiation generation apparatus 300. It is assumed that the change of the photographing period managed by the frame rate management unit 116 is performed during a period from the power-on to the sensing of the radiation irradiation. When the current value changes and the irradiation of the radiation is sensed by the exposure sensing unit 243, the flow advances to Step S303 so that the sensing of the radiation using the power supply circuit 240 performed by the control unit 101 is stopped.

<From Radiation Irradiation to Photographing>

After the stop of radiation sensing, the flow advances to Step S304, and processing of monitoring the increase and decrease in irradiation dose by the irradiation dose measurement unit 115, more specifically, the determination unit 117, through use of the detection pixel 204 and the detection drive line 211 is started. After the irradiation dose monitoring is started, the flow advances to Step S305. In Step S305, the image acquisition control unit 103 starts the fluoroscopy of the subject. In the first embodiment, fluoroscopy in which the radiation generation apparatus 300 performs pulse irradiation of radiation is carried out, but the mode of the irradiation of radiation may be continuous irradiation. In the first embodiment, the detection drive line 211 is used to monitor the irradiation dose, but the detection pixel 204 may be individually operated to monitor the dose. As another example, without using the detection drive line 211 or the detection pixel 204, another irradiation dose measurement unit may be provided, and the dose may be monitored through use of this unit.

<During Photographing>

Figure 4:
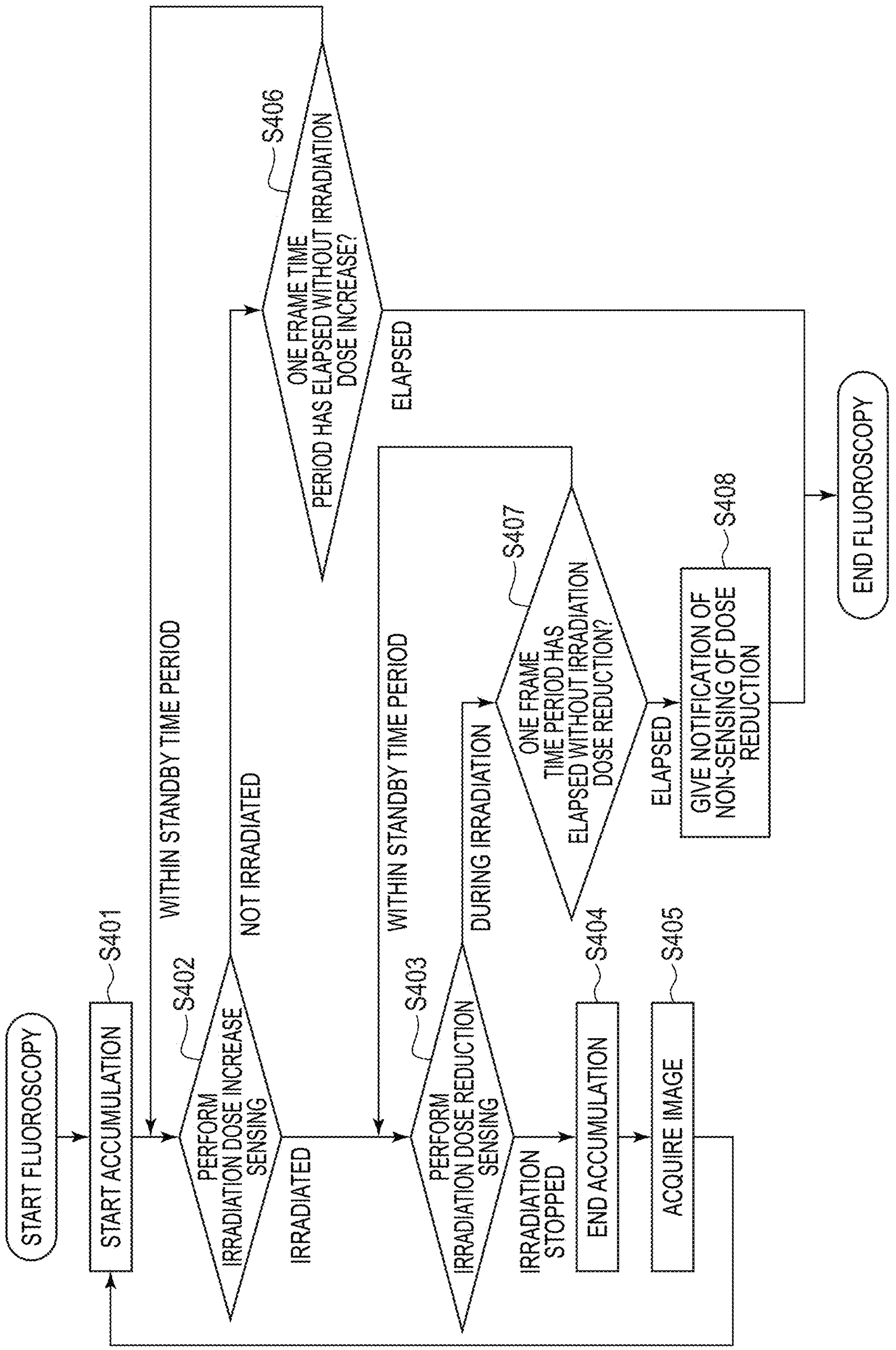
FIG. 4 is a flow chart for illustrating a photographing operation of the fluoroscopy in the flow chart of FIG. 3.

Next, with reference to FIG. 4, processing of fluoroscopy performed in Step S305 is described. FIG. 4 is a flow chart for illustrating the photographing operation of the fluoroscopy. When the fluoroscopy is started, the flow advances to Step S401. In Step S401, first, the image acquisition control unit 103 starts an accumulation operation of accumulating electric charges by each pixel of the radiation detection unit 200. When the accumulation operation is started, the flow advances to Step S402.

After the accumulation is started, in Step S402, the determination unit 117 monitors an increase amount of the irradiation dose in the detection pixel 204 through use of the detection drive line 211. When the determination unit 117 senses the increase amount of the irradiation dose of an increase threshold value or more, it is determined that the irradiation of radiation is performed, and the image acquisition control unit 103 advances the flow to Step S403. When the determination unit 117 senses that the increase amount of the irradiation dose is smaller than the increase threshold value, it is determined that no irradiation of radiation is performed, and the image acquisition control unit 103 advances the flow to Step S406.

In Step S406, the image acquisition control unit 103 determines whether or not a time period corresponding to one frame rate has elapsed from the start of accumulation based on information on the frame rate (photographing period) managed by the frame rate management unit 116. When it is determined that the time period corresponding to one frame rate has not elapsed, the flow returns to Step S402, and the determination unit 117 re-monitors the increase amount of the radiation dose. This increase threshold value may be a fixed value or a variable value. When it is determined that the time period corresponding to one frame rate has elapsed, it is determined that the irradiation of radiation to the subject is not performed, and thus the fluoroscopy is ended. When it is determined that the time period corresponding to one frame rate has elapsed in Step S406 after the flow has gone through Step S405 to be described later, the image taken last is stored in the image data storage portion 107 as photographing data, and the fluoroscopy is ended.

In Step S403, the determination unit 117 monitors a reduction amount of the irradiation dose in the detection pixel 204 through use of the detection drive line 211. When the determination unit 117 senses the reduction amount of the irradiation dose of a reduction threshold value or more, it is determined that the irradiation of radiation has stopped, and the image acquisition control unit 103 advances the flow to Step S404.

In Step S403, when the determination unit 117 senses that the reduction amount of the irradiation dose is smaller than the reduction threshold value, it is determined that the irradiation of radiation is performed, and the image acquisition control unit 103 advances the flow to Step S407. In Step S407, the image acquisition control unit 103 determines whether or not the time period corresponding to one frame rate has elapsed from the start of accumulation based on the information on the frame rate (photographing period) managed by the frame rate management unit 116. When it is determined that the time period corresponding to one frame rate has not elapsed, it is determined that the accumulation operation is executed. Thus, the flow returns to Step S403, and the reduction amount of the radiation dose is re-monitored. When it is determined that the time period corresponding to one frame rate has elapsed, the image acquisition control unit 103 advances the flow to Step S408.

When it is determined in Step S407 that the time period corresponding to one frame rate has elapsed, it can be determined that no irradiation dose reduction has been sensed while the radiation generation apparatus 300 performs pulse irradiation of radiation. In this case, the drive control unit 102 stores the image taken last into the image data storage portion 107, and, in Step S408, for example, the drive control unit 102 uses the display monitor 500 or the like to notify the user of the non-sensing of the irradiation stop, and ends the fluoroscopy. The method of notifying the user of the non-sensing is not limited to the mode using the display monitor 500, and publicly-known notification methods such as a buzzer and a voice message can be used.

In Step S404, the image acquisition control unit 103 ends the accumulation operation in the radiation detection unit 200. When the stop of the radiation irradiation is detected in Step S403 and the accumulation operation is ended in accordance therewith, the stop of the radiation irradiation is synchronized between the radiation generation apparatus 300 and the radiation imaging apparatus 100. The threshold value of the reduction amount of the radiation dose in Step S403 may be a fixed value or a variable value. After the accumulation operation is ended, the image acquisition control unit 103 advances the flow to Step S405 to execute readout of the accumulated electric charges to acquire an image. When the image acquisition for one frame performed by the image acquisition control unit 103 is ended in Step S405, the flow returns to Step S401, and the process steps of the subsequent steps are repeated.

<After Photographing>

After the fluoroscopy is ended, the drive control unit 102 advances the flow from Step S305 of FIG. 3 to Step S306 to stop the irradiation dose monitoring using the detection drive line 211. In Step S306, which continues from Step S305, the drive control unit 102 further determines whether or not an instruction to continuously perform photographing after the irradiation dose monitoring using the detection drive line 211 is stopped has been received from the control apparatus 400 (Step S307). Then, when it is determined that the instruction to perform photographing has been given, the flow returns to Step S301, and an operation of sensing the radiation irradiation using the power supply circuit 240 described above is re-started for standby for the next photographing. When it is determined that no instruction to perform photographing has been given, the photographing is directly ended.

In the first embodiment, the determination of photographing continuation is made after the monitoring of the increase and decrease in irradiation dose using the detection drive line 211 is stopped, but the operation of sensing the radiation using the power supply circuit 240 may be started without performing particular determination. Further, not the control apparatus 400 but the radiation imaging apparatus 100 may have an input device for inputting a photographing instruction, and the operation of sensing the radiation using the power supply circuit 240 may be started based on the instruction of this input device.

In general, in radiation photographing, the radiation irradiation apparatus and the radiation imaging apparatus perform synchronous communication to operate at synchronized timings. Even when no synchronous communication is performed, both the apparatus are required to operate at synchronized timings, but the timings are gradually shifted due to the difference in timing management accuracy between both the apparatus, and hence rate adjustment is also required. For example, in a case in which an irradiation section and readout start processing overlap each other, when the readout processing is restarted, whether out-of-synchronization has been caused can be determined with reference to whether electric charges have been accumulated in a corresponding part. In such a method, whether the apparatus operate in synchronization is constantly checked, and the determination of the start and the end of the photographing is made by transmitting a signal for notification of the timing. In such a case, power consumption for synchronization is increased and hence the battery consumption is increased, with the result that photographing cannot be performed unless the apparatus are synchronized.

Through use of the configuration according to the present disclosure, the irradiation start can be sensed by sensing the change in bias current operating with electric power lower than electric power used when the irradiation dose sensing is executed. Accordingly, the irradiation sensing can be performed with reduced power consumption during photographing standby, which leads to improvement in usage time of the battery of the radiation imaging apparatus. Moreover, because the determination of the photographing end can be made, which image is the image acquired last can be known, and thus last image hold of displaying the last image at the time of end of the fluoroscopy can be performed. Further, the end of the photographing can be reliably grasped, and hence the shift to the drive of the photographing standby for the next photographing can be performed immediately after the last photographing. Further, the irradiation dose sensing and the determination of the end of the moving-image photographing using the frame rate are performed, and thus the photographing drive can be stopped in a short time period after the photographing. Thus, effects such as reduction in power consumption and image quality improvement because of becoming easier to ensure a time period for preparation for the next photographing, for example, correction data update can be obtained. For example, when the change in photographing operation state is large such as when the still-image photographing is subsequently performed after the fluoroscopy, a time period for preparation drive in an operation environment of new photographing (in this example, the still-image photographing) is required. Thus, it is required to promptly end the current photographing (in the case of this example, the fluoroscopy), and hence the photographing end determination of the present technology is effective. The end of the moving-image photographing means the end of the continuous irradiation of the pulse radiation (end of the irradiation of the pulse radiation in a certain frame rate).

Modification Example of First Embodiment

In the first embodiment, description is given of a case in which the pulse irradiation of the radiation is performed, and image data of one frame is obtained in accordance with one pulse irradiation. In contrast, in this modification example, description is given of a case in which fluoroscopy of performing continuous irradiation of radiation is performed. Regarding the configurations described in the first embodiment and each step of the flow chart at the time of photographing, the same or similar parts as or to those of the first embodiment are denoted by the same reference symbols or the like to omit a detailed description thereof here.

Figure 5:
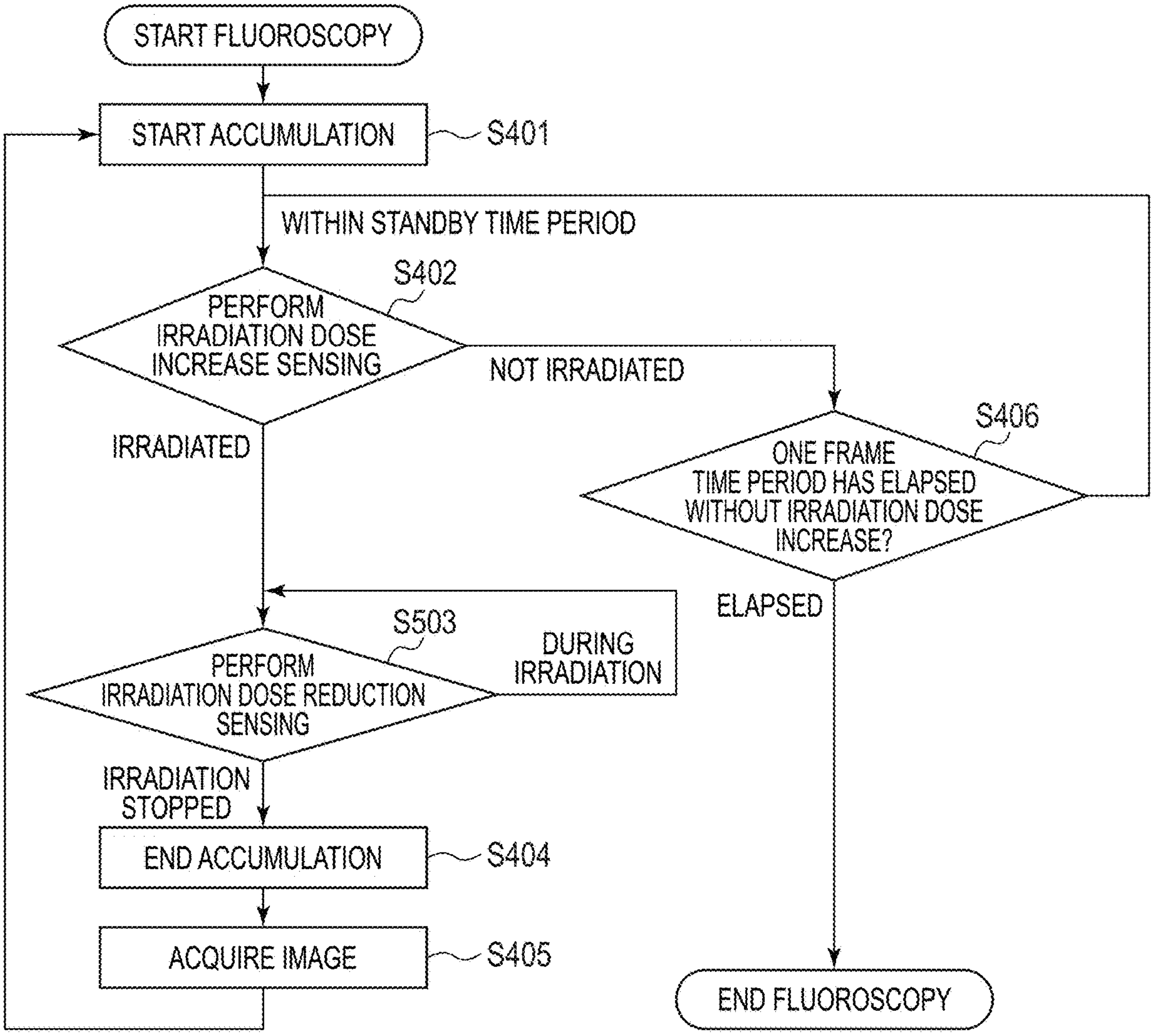
FIG. 5 is a flow chart for illustrating a photographing operation of fluoroscopy using continuous irradiation of radiation in the first embodiment.

This modification example is different from the first embodiment in the process step corresponding to Step S403 in the fluoroscopy of the first embodiment. Here, this different process step is described. The process steps in the other steps performed at the time of fluoroscopy are similar to the process steps of the first embodiment illustrated in FIG. 4. In this modification example, as illustrated in FIG. 5, instead of Step S403, processing of comparing the reduction amount of the radiation dose with a threshold value shown in Step S503 is performed. Specifically, the irradiation dose measurement unit 115 uses the detection drive line 211 to monitor the reduction amount of the irradiation dose in the detection pixel 204. When the determination unit 117 senses the reduction amount of the irradiation dose of a threshold value or more, it is determined that the irradiation of radiation has stopped, and the image acquisition control unit 103 advances the flow to Step S404. The subsequent process steps and the threshold value are similar to those described in the first embodiment.

When the determination unit 117 senses that the reduction amount of the irradiation dose is smaller than the threshold value, it is determined that the irradiation of radiation is continued, and the process step of Step S503 is repeated again. The process step of Step S503 is repeated until the reduction amount of the irradiation dose of the threshold value or more is sensed by the irradiation dose measurement unit 115. With such a process step being executed, image data can be acquired by continuous irradiation of radiation.

Second Embodiment

In the above-mentioned first embodiment, after the radiation imaging apparatus 100 is activated, the start of the fluoroscopy is determined based on the radiation sensing using the power supply circuit 240. However, an application example of the present disclosure is not limited thereto. In the configuration of the radiation imaging apparatus 100 and the like described in the first embodiment, the fluoroscopy may be started by monitoring the irradiation dose from the first time through use of the detection pixel 204 and the detection drive line 211 to sense the irradiation dose increase.

However, when the irradiation dose monitoring is constantly performed, the power consumption is increased. Accordingly, it is desired in terms of power consumption to determine the start of the fluoroscopy through the radiation sensing having a small power consumption in the first time.

As described above, the radiation imaging apparatus 100 according to one embodiment of the present disclosure includes the radiation detection unit 200, a sensing unit (243), and the determination unit 117. The radiation detection unit 200 includes a plurality of pixels 201 and 204 for radiation detection arranged therein and is to be used for generation of image data based on radiation applied to the radiation detection unit 200. The sensing unit exemplified by the exposure sensing unit 243 senses that the irradiation of the radiation from the radiation source 301 has started based on the change in bias current supplied to the plurality of pixels 201 and 204. The determination unit 117 determines that the irradiation of the radiation has stopped when the reduction amount of the irradiation amount of the radiation obtained from the detection pixel 204 included in the plurality of pixels 201 and 204 is larger than the reduction threshold value. As described above, when the sensing unit senses that the radiation irradiation has started and the determination unit 117 senses that the radiation irradiation has stopped, those start and stop timings can be identified. With those configurations, in particular, the timing of the stop of the pulse irradiation of the radiation can be identified, and hence photographing of the radiation image corresponding to the pulse irradiation of the radiation can be performed even without performing synchronous communication.

Further, the above-mentioned radiation imaging apparatus 100 can further include the frame rate management unit 116 for managing the frame rate regarding the timing to acquire the image data. When the increase amount of the irradiation amount of the radiation obtained from the detection pixel 204 is smaller than the increase threshold value, the determination unit 117 determines that the irradiation of the radiation is not performed. At this time, when the determination that the irradiation is not performed is not changed within one frame time period managed by the frame rate management unit 116, the determination unit 117 can generate an instruction to end acquisition of the image data for the image acquisition control unit 103. In addition, when the determination that the irradiation is not performed is changed within the frame rate, the determination unit 117 can determine whether the reduction amount of the irradiation amount of the radiation obtained from the detection pixel 204 is larger than the reduction threshold value. In the present disclosure, as described above, after the sensing unit senses the irradiation of the radiation, further, through use of the detection pixel 204, the state of the irradiation of the radiation, specifically, the fact of irradiation is first checked with reference to the frame rate. The power supply circuit 240 supplies the bias voltage and the refresh voltage to the plurality of pixels 201 and 204 through use of the same bias line 230. In addition, at the time of sensing of the radiation irradiation, the power supply circuit 240 sequentially performs the refresh operation and the operation of monitoring the current of the bias line for each pixel column. Accordingly, when the operation of monitoring the bias current is performed after the acquisition of the image data is started, there is a possibility that the image data of each column may be damaged. As described above, when there is employed a configuration in which, after the start of the radiation irradiation is sensed by the sensing unit, continuation of the radiation irradiation or the like is checked through use of the detection pixel 204, the exposure sensing unit 243 is stopped, and thus the possibility of such data damage can be eliminated.

Moreover, when the determination unit 117 determines that the irradiation is not performed within the frame rate, the determination unit 117 determines whether the increase amount of the irradiation amount of the radiation obtained from the detection pixel 204 is smaller than the increase threshold value, within the frame rate after the determination. In this case, when it is determined that the increase amount is equal to or larger than the increase threshold value, the generation of the image data by the radiation detection unit 200 is continued. In addition, when the reduction amount of the irradiation amount of the radiation obtained from the detection pixel 204 is smaller than the reduction threshold value, the determination unit 117 determines that the irradiation of the radiation is performed. Further, when the determination that the irradiation is performed is not changed within the frame rate managed by the frame rate management unit 116, the determination unit 117 can generate an instruction to end acquisition of the image data for the image acquisition control unit 103. Moreover, when the instruction to end the acquisition of the image data is generated, the radiation imaging apparatus 100 can further include a unit for notifying the user of the non-sensing of the stop of the irradiation of the radiation, such as the display monitor 500.

The radiation imaging apparatus 100 according to one embodiment of the present disclosure described above further includes a control unit (drive control unit 102) for controlling the operation of the sensing unit. When the sensing unit senses that the irradiation of the radiation has started, the control unit stops the operation of the sensing unit. In addition, the determination unit 117 determines the state of the irradiation of the radiation under a state in which the operation of the sensing unit is stopped. As described above, it cannot be said that execution of the operation of monitoring the bias current after the acquisition of the image data is started is appropriate. When the sensing operation of the sensing unit is stopped by the control unit as described above, the possibility of such data damage can be eliminated. Further, in some cases, the determination that the irradiation is not performed is not changed within the managed frame rate after the reduction amount of the irradiation amount of the radiation is larger than the reduction threshold value and the determination unit 117 determines that the irradiation of the radiation has stopped. In such cases, the control unit operates the sensing unit for standby for the next radiation irradiation. Accordingly, photographing in the next frame can be continuously performed at the time of pulse irradiation.

Further, in the radiation imaging apparatus 100 according to one embodiment of the present disclosure described above, the detection pixel 204 is arranged in the radiation detection unit 200 as a pixel other than pixels (other than the pixels 201) to be used for generation of the image data in the plurality of pixels 201 and 204 which are two-dimensionally arranged. The detection pixel 204 may be provided at a specific position or may be randomly arranged in the pixels which are two-dimensionally arranged. Further, the number of the detection pixels 204 is also not particularly limited. Further, the image data cannot be obtained from the part in which the detection pixel 204 is arranged, but the image data corresponding to this pixel can be generated by a publicly-known interpolation technology or the like, and this image data can be used.

Further, one embodiment of the present disclosure can provide a radiation imaging apparatus 100 capable of performing moving-image photographing by receiving radiation that is continuously applied in a pulse form (hereinafter referred to as "pulse radiation"). This radiation imaging apparatus 100 capable of performing moving-image photographing includes a conversion element (220, 225), an acquisition unit (image acquisition control unit 103), a readout unit (readout circuit 260), and the determination unit 117. The conversion element can generate electric charges in accordance with irradiation of the pulse radiation. The readout unit reads out the electric charges generated by the conversion element. The image acquisition control unit 103 exemplified as one mode of the acquisition unit can acquire information on the frame rate of the moving-image photographing, which is managed by the frame rate management unit 116. The determination unit 117 can determine the end of the moving-image photographing based on the change in electric charges read out by the readout unit and the information on the frame rate acquired by the acquisition unit.

In such a configuration, the information on the frame rate can include a time period (one frame time period) required for acquiring one frame. In such a case, the determination unit 117 can determine that the moving-image photographing has ended when the one frame time period has elapsed without the increase amount of the electric charges read out by the readout unit exceeding the threshold value. Further, the determination unit 117 can determine the stop of the irradiation of the pulse radiation. In such a case, the readout unit can determine the stop of the irradiation of the pulse radiation based on the change in the read-out electric charges. In more detail, the determination unit 117 can determine the stop of the irradiation of the pulse radiation when the reduction in electric charges read out by the readout unit exceeds a threshold value. Moreover, the determination unit 117 can also determine the start of the moving-image photographing. In such a case, the determination unit 117 can determine the start of the moving-image photographing based on the change in bias current supplied to the plurality of pixels.

Further, the present disclosure can provide the radiation imaging system 1. In this case, the radiation imaging system 1 includes the above-mentioned radiation imaging apparatus 100, and the radiation generation apparatus 300 that can emit radiation independently of the radiation imaging apparatus 100. Further, the present disclosure can also provide an operation method of causing the radiation imaging apparatus 100 to perform the processing executed for the above-mentioned radiation detection unit 200 by the sensing unit (243) and the determination unit 117.

As described above, according to the radiation imaging apparatus of the present disclosure, before the photographing is started, the power supply circuit 240 is driven and is used to sense the start of the radiation irradiation. Then, after the radiation irradiation is sensed and it is determined that the photographing has started, the detection pixel 204 and the detection drive line 211 are used to monitor the irradiation dose, and the photographing end is determined. With the start and the end of the photographing being determined as described above, the radiation photographing can be carried out without performing synchronous communication. Further, when the detection pixel 204 and the detection drive line 211 are used to perform irradiation dose monitoring only during photographing, the power consumption during the photographing standby can be reduced. Further, when the detection pixel 204 and the detection drive line 211 are used to monitor the irradiation dose so that the end of the photographing is determined, the operation can be promptly shifted to standby drive for the next photographing. Moreover, the photographing end can be determined, and thus the last image can be determined. As a result, last image hold of displaying the last image at the time of end of the fluoroscopy can be performed.

According to one embodiment of the present disclosure, in the radiation imaging apparatus, it is possible to perform imaging processing of determining the end of fluoroscopy without performing synchronous communication to and from the radiation generation apparatus.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The processors or circuits can include a central processing unit (CPU), a micro processing unit (MPU), a graphics processing unit (GPU), an application-specific integrated circuit (ASIC), or a field-programmable gate array (FPGA). The processors or circuits can also include a digital signal processor (DSP), a data flow processor (DFP), or a neural processing unit (NPU).

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

Further, the above-mentioned embodiments and modification examples may be combined with each other as appropriate within the scope not deviating from the gist of the present disclosure.

This application claims the benefit of Japanese Patent Applications No. 2023-156560, filed Sep. 21, 2023, and No. 2024-115665, filed Jul. 19, 2024, which are hereby incorporated by reference herein in their entirety.

What is claimed is:

1. An x-ray radiation imaging apparatus which is configured to perform moving-image photographing by receiving continuous irradiation of pulse x-ray radiation, the x-ray radiation imaging apparatus comprising:

a conversion element configured to generate electric charges in accordance with irradiation of the pulse x-ray radiation;

an acquisition unit configured to acquire information on a frame rate of the moving-image photographing;

a readout unit configured to read out the electric charges generated by the conversion element; and a determination unit configured to determine end of the moving-image photographing based on a change in the electric charges read out by the readout unit, and the information on the frame rate acquired by the acquisition unit.

2. The x-ray radiation imaging apparatus according to claim 1, wherein the information on the frame rate acquired by the acquisition unit is a one frame time period, and wherein the determination unit is configured to determine that the moving-image photographing has ended when the one frame time period has elapsed without an increase amount of the electric charges read out by the readout unit exceeding a threshold value.

3. The x-ray radiation imaging apparatus according to claim 1, wherein the determination unit is configured to determine stop of the irradiation of the pulse x-ray radiation, and to determine the stop of the irradiation of the pulse x-ray radiation based on the change in the electric charges read out by the readout unit.

4. The x-ray radiation imaging apparatus according to claim 3, wherein the determination unit is configured to determine that the irradiation of the pulse x-ray radiation has stopped when reduction in the electric charges read out by the readout unit exceeds a threshold value.

5. The x-ray radiation imaging apparatus according to claim 1, wherein the determination unit is configured to determine start of the moving-image photographing, and to determine the start of the moving-image photographing based on a change of a bias current supplied to a plurality of pixels.

6. An-x-ray radiation imaging system comprising:

the x-ray radiation imaging apparatus according to claim 1; and a processing apparatus configured to acquire image data from the x-ray radiation imaging apparatus to process the acquired image data.

7. An x-ray radiation imaging apparatus comprising:

a radiation detection unit which includes a plurality of pixels for x-ray radiation detection arranged therein and which is to be used for generation of image data based on x-ray radiation applied to the radiation detection unit;

a sensing unit which senses that the irradiation of the x-ray radiation has started based on a change in a bias current supplied to the plurality of pixels; and a determination unit configured to determine that irradiation of the x-ray radiation has stopped when a reduction amount of the irradiation amount of the x-ray radiation obtained from a detection pixel included in the plurality of pixels is larger than a reduction threshold value, wherein the determination unit determines that irradiation of the x-ray radiation has stopped based on a case in which a state where the reduction amount of the irradiation amount of the x-ray radiation obtained from the detection pixel included in the plurality of pixels is larger than a reduction threshold value continues for a predetermined time period.

8. The x-ray radiation imaging apparatus according to claim 7, further comprising:

a frame rate management unit configured to manage a frame rate regarding a timing to acquire the image data; and a control unit configured to control an operation of the sensing unit, wherein the control unit is configured to stop the operation of the sensing unit when the sensing unit senses that the irradiation of the x-ray radiation has started, and wherein the determination unit is configured to perform the determination under a state in which the operation of the sensing unit is stopped.

9. The x-ray radiation imaging apparatus according to claim 8, wherein the predetermined time period is a one frame time period.

10. The x-ray radiation imaging apparatus according to claim 7, further comprising:

a frame rate management unit configured to manage a frame rate regarding a timing to acquire the image data; and a control unit configured to control an operation of the sensing unit, wherein the control unit is configured to operate the sensing unit for standby for next x-ray radiation irradiation when determination that the irradiation is not performed is not changed within the frame rate managed by the frame rate management unit after the determination unit determines that the reduction amount of the irradiation amount of the x-ray radiation is larger than the reduction threshold value and the irradiation of the x-ray radiation has stopped.

11. An x-ray radiation imaging system comprising:

the x-ray radiation imaging apparatus according to claim 7; and a processing apparatus configured to acquire image data from the x-ray radiation imaging apparatus to process the acquired image data.

* * * * *